(12) United States Patent
Keep et al.

(10) Patent No.: US 7,446,093 B1
(45) Date of Patent: Nov. 4, 2008

(54) CEREBROSPINAL AND VASCULAR PHARMACEUTICAL COMPOSITION AND PROCESS FOR PREPARING THE SAME

(75) Inventors: Marcus Keep, Honolulu, HI (US); Eskil Elmer, Lund (SE)

(73) Assignee: Maas BiolAB, LLC, Albuquerque, NM (US)

( * ) Notice: Subject to any disclaimer, the term of this patent is extended or adjusted under 35 U.S.C. 154(b) by 0 days.

(21) Appl. No.: 09/674,092

(22) PCT Filed: Feb. 26, 2000

(86) PCT No.: PCT/US99/04359

§ 371 (c)(1),
(2), (4) Date: Aug. 26, 2002

(87) PCT Pub. No.: WO00/50058

PCT Pub. Date: Aug. 31, 2000

(51) Int. Cl.
*A61K 38/12* (2006.01)
*A61K 38/00* (2006.01)

(52) U.S. Cl. ............................. 514/9; 514/11; 530/317
(58) Field of Classification Search .................... 514/9, 514/11; 530/317
See application file for complete search history.

(56) References Cited

U.S. PATENT DOCUMENTS

| 4,649,047 | A |   | 3/1987 | Kaswan |       |
|-----------|---|---|--------|--------|-------|
| 5,221,607 | A | * | 6/1993 | Cordell et al. | 435/6 |
| 5,252,463 | A | * | 10/1993 | Nelson et al. | 435/23 |
| 5,807,820 | A |   | 9/1998 | Elias |       |
| 5,811,410 | A |   | 9/1998 | Falk et al. | 514/54 |
| 5,827,834 | A | * | 10/1998 | Falk et al. | 514/54 |

OTHER PUBLICATIONS

Lebel et al., Int. Arch. Allergy. Immunol., vol. 116, pp. 284-287, 1998.*
Kessler te al., Biochemical Pharmcaology, vol. 40, No. 1, pp. 169-173, 1990.*
Ezzel, Scientific America, pp. 152-153, Mar. 7, 1993.*
Varon et al., Dev. Neurosci., vol. 6, pp. 73-100, 1983/1984.*
Okonkwo et al. An Intrthecal Bolus of Cyclosporin A Before Injury Preserves Mitcohohdrial Integrity and Attenuates Axonal Disruption in Traumatic Brain Injusry, 1999, J. cereb. Blood Flow Metab., vol. 19, No. 4, pp. 443-451.*
Pubmed Abstract 9693278, Lebel et al., "Inhibition of mediator release from dispersed nasl polyp cells by cyclosporin A," Aug. 1998, Int Arch Allery Immunol, vol. 116, No. 4, pp. 284-287.
Pubmed Abstract 2164815, Kessler et al., "Complexation and medium effects on the conformation of cyclosporin A studied by NMR spectroscopy and molecular dynamics calculation," Jul. 1, 1990, Biochem Pharmacol, vol. 40, No. 1, pp. 169-173.
Shimizu et al., "Dimethylsulfoxide (DMSO) treatment reduces infarction vol. after permanent focal cerebral ishchemia in rats," Neuroscience Letters, vol. 239, No. 2-3, Dec. 19, 1997, pp. 125-127, XP-002316700.
Elzinga et al., "The Effect of Dimethyl Sulfoxide on the Absorption of Cyclosporine in Rats," Transplantation, vol. 47, No. 2, Feb. 1989, pp. 394-395, XP009043582.
Broadwell et al., "Morphologic Effect of Dimethyl Sulfoxide in the Blood-Brain Barrier," Science, vol. 217, No. 4555, Jul. 9, 1982, pp. 164-166, XP009043581.

* cited by examiner

*Primary Examiner*—Jon P Weber
*Assistant Examiner*—Abdel A Mohamed
(74) *Attorney, Agent, or Firm*—Birch, Stewart, Kolasch & Birch, LLP

(57) ABSTRACT

A cyclosporin-containing pharmaceutical preparation for cerebrospinal or vascular application is disclosed, comprising (1) at least one cyclosporin, and (2) DMSO.

10 Claims, No Drawings

CEREBROSPINAL AND VASCULAR PHARMACEUTICAL COMPOSITION AND PROCESS FOR PREPARING THE SAME

This application is the national phase under 35 U.S.C. § 371 of PCT International Application No. PCT/US99/04359 which has an International filing date of Feb. 26, 1999, which designated the United States of America.

1. Field of the Invention

This invention relates to pharmaceutical compositions that facilitate the administration of cyclosporins, particularly into cerebrospinal and vascular fluid spaces.

2. Background Art

Cyclosporin A and Derivatives.

Cyclosporin A is an immunosuppressive drug. The above mentioned treatment medication has already been described, in U.S. Pat. No. 4,117,118 and numerous patents since, which relate to its production, formulation and immunosuppressive properties.

Cyclosporin A is a product of the fungus Tolypocladium Inflatum Gams. It is a cyclic poly-amino acid molecule, consisting of 11 amino acids. One of the amino acids is unique for cyclosporin A, a β-hydroxyamino acid called butenyl-methyl-threonin (MeBmt). The molecular weight is 1202.6 and the chemical composition is $C_{62}H_{111}N_{11}O_{12}$.

The molecule is highly lipophilic, and therefore virtually insoluble in water. The drug is transported in the blood within red blood cells to about 58%, and the remaining approximately 10–20% in leukocytes, and 33% bound to plasma proteins. In the plasma cyclosporin A is bound to high-density lipoprotein, low-density lipoproteins, very-low density lipoproteins and a small fraction to albumin. A very small fraction is free in plasma.

The drug undergoes extensive metabolism, mainly in the liver by the cytochrome P450 system. There are at least 30 known metabolites of cyclosporin A, with various chemical modifications, such as hydroxylation, demethylation, oxidation and epoxide formations. There are a number of variants of cyclosporin A, differing for example in one amino acid, which have similar pharmacological properties. Under normal conditions, cyclosporin A and its metabolites do not pass the blood-brain barrier. When the glycoprotein-p transporter is poisoned, or the blood-brain barrier is disrupted, cyclosporin is able to cross it and come into contact with neurons. Several analogs of cyclosporin are able to readily cross the blood-brain barrier. Several analogs of cyclosporin are not immunosuppressants. There is a subset of analogs of cyclosporin that both readily cross the blood-brain barrier and are not immunosuppressants.

The family of cyclosporins includes cyclosporin A, cyclosporin C, cyclosporin D, and cyclosporin G. Some known metabolites of cyclosporin A include the following: (according to Hawk's Cay nomenclature) AM1, AM9, AM1c, AM4N, AM19, AM1c9, AM1c4N9, AM1A, AM1A4N, AM1Ac, AM1AL, AM11d, AM69, AM4N9, AM14N, AM14N9, AM4N69, AM99N, Dihydro-CsA, Dihydro-CsC, Dihydro-CsD, Dihydro-CsG, M17, AM1c-GLC, sulphate conjugate of cyclosporin, BH11a, BH15a, B, G, E, (and with come overlap with the Hawk's above, according to Maurer's nomenclature) M1, M2, M3, M4, M5, M6, M7, M8, M9, M10, M11, M12, M13, M14, M15, M16, M17, M18, M19, M20, M21, M22, M23, M24, M25, M26, MUNDF1 and MeBMT. Some metabolites of cyclosporin G include GM1, GM9, GM4N, GM1c, GM1c9, and GM19. Modified cyclosporins include modified C-9 amino acid analogs, modified 8-amino acid analogs, modified 6-position analogs containing MeAla or MeAbu residue, and SDZ 209-313, SDZ-205-549, SDZ-033-243, and SDZ-PSC-833.

This entire family of cyclosporins, including cyclosporin A, all derivatives, variants, amino acid variants, metabolites, including variations of mono-, di- and trihydroxylates, N-demethylates, aldehydes, carboxylates, conjugates, sulphates, glucuronides, intramolecular cyclizations and those without a cyclic structure as well as shorter peptides and amino acids and their derivatives and salts with or without immunosuppressive properties and whether able to cross the blood brain barrier or not will hereinafter be referred to as cyclosporin or cyclosporins.

Cyclosporins are highly lipophilic and virtually insoluble in water. They require an emulsifier to remain in aqueous phase, such as cremophore or Labrafil. One problem is that these emulsifiers are anaphylactic, and are neurotoxic. There is a need for an improved formulation for intravenous and oral use that is neither anaphylactic nor neurotoxic.

Further no formulation in existence is suitable for injection into the cerebrospinal fluid or the brain because of the neurotoxic and irritant properties of the emulsifiers. No formulation now exists which is used for cerebrospinal administration.

Therefore our aim was to create a unique cerebrospinal pharmaceutical composition with cyclosporin as the active ingredient that does not contain dangerous neurotoxic emulsifiers and irritants found in vascular and oral formulations.

Now we have found that if cyclosporin is dissolved in DMSO (dimethyl sulfoxide), the neurotoxic and irritant effects on the nervous system are not seen. Further we have found that not only is it a unique new cerebrospinal fluid composition with great safety and free from neurotoxicity, but that it is also an improve formulation for intravascular and oral administration too.

DMSO

Dimethyl sulfoxide is an industrial solvent derived from wood. It is biocompatible, but approved in only one condition for human use, that of interstitial cystitis, a completely unrelated bladder condition. DMSO may by itself be useful for other conditions such as scleroderma, arthritis, mental illness, and brain trauma, but is not accepted into general medical use for these conditions.

The Instant Invention.

Cyclosporins are highly lipid soluble. There are well known to the art a number of mixtures for oral and intravenous administration, usually involving a carrier solution of lipid in water emulsion, micro-emulsion or nano-emulsion or particles. For intravenous administration this lipid in water emulsion is designed to allow administration in fluid phase mixed with salt-water solution to allow easy flow without precipitation of cyclosporin in the administering tubing or the blood. This has been acceptable in the past for simple intravenous (or oral) administration at the relatively low doses needed to treat immune rejection in transplantation or autoimmune disease.

It has been recently discovered that cyclosporin is neuroprotective when it comes into contact with neurons. Since the drugs are also systemically immunosuppressive, it would be desirable to administer them selectively into the brain or the cerebrospinal fluid around the brain. Nonsystemic local CSF administration of cyclosporin would reduce systemic immune suppression, and increase brain and spine neuron exposure compared to systemic administration, both very desirable goals in patients in need of neuroprotection but not in need of immunosuppression. Especially patients that need long term treatment neuroprotection (such as those with amyotrophic lateral sclerosis, Parkinson's disease and Alzheimer's disease), it is desirable to avoid the complication, or undesirable side effect of lifelong systemic immunosuppression.

Lipids emulsifiers are used in Sandimmune (Novartis' formulation for cyclosporin) such as a modified castor oil derivative (Labrafil and cremophore). These castor oil derivatives have beep themselves found to be directly neurotoxic, and likely to be the cause of the reported cases of neurologic problems of encephalopathy, and seizures in transplant patients.

Other formulations use less neurotoxic lipid formulations such as toceraphols. However lipids injected into the cerebrospinal fluid have been reported to cause severe complications of archnoiditis or inflammation around the spinal cord- such as the discontinued oil based Pantopaque intrathecal X-ray contrast used in spinal myelograms. Injecting lipids, even in micro or nano-emulsions into the cerebrospinal spaces would likely cause layering of the lipid, since the long column of fluid in the spine contains slow moving CSF, which is a very different milieu than the rapidly flowing and mixing turbulent arterial and venous blood. The layering of lipid and drug in the cerebrospinal fluid column would result in undesirable cyclosporin over or underdosage, depending on location.

In addition, ethanol is a commonly used solvent for cyclosporin used in Sandimmune, and SangCya (Sangstat's cyclosporin formulation). Ethanol is a known neurotoxin, and is used for neurolysis or destruction of nerve roots by injection into the brain or cerebrospinal fluid spaces.

It is now found to be desirable to inject cyclosporin into the fluid contained within the brain, mid in which the brain floats, the cerebrospinal fluid. Clearly all previously described oral preparations, and all previously described intravenous preparations are not suitable because they contain neurotoxins and irritants as solvents or emulsifiers. In addition the known intravenous formulations are not ideal for intravenous use because they contain neurotoxins which causes the documented manifestations of neurotoxicity in patients obtaining intravenous or oral administration. Cerebrospinal injections of these intravenous formulations would cause unacceptable and potentially lethal neurotoxic effects.

All previous formulations for cyclosporin have utilized a lipid emulsifier to obtain solubility. It would not be expected by a person skilled in the art that a completely different class of compound other than a lipid emulsifier, such as the industrial solvent DMSO would turn out to be suitable for intracerebrospinal administration. Further they would not expect that the use of an industrial solvent would be an improvement over existing intravascular and oral cyclosporin compositions.

This novel formulation for administering cyclosporin into the CSF is the use of dimethylsulfoxide (DMSO) as the carrier medium or solvent. Cyclosporin is very soluble in DMSO. Unlike castor oil derivatives or ethanol, DMSO is not neurotoxic. It is highly biocompatible and is actually a known neuroprotectant in its own right. It is possible to safely administer DMSO. DMSO prevents precipitation of cyclosporin even when diluted in the CSF.

In addition DMSO easily crosses tissues barriers in its role as a solvent and carries in with it drugs dissolved in it. This is an advantage because it opens the blood-brain barrier and CSF-brain barrier to facilitate cyclosporin penetration into the brain.

The two main methods for infusing the formulation will be via the cerebral ventricles and the thecal sac. A catheter placed through a scalp incision, a skull twist drill hole and the brain, will access the cerebral ventricles. If a short-term infusion of several days is desired the catheter would be remain externalized and then removed. If a long term infusion over months or years were desired, the skin would be closed over the catheter and an attached refillable reservoir or drug pump.

Thecal sac infusion is typically by lumbar puncture in the lumbar spine (or less often at the top of the spine at the base of the skull). The spinal puncture needle is placed through the skin of the back and pierces the dura (thecal sac) which contains the CSF in which the spinal cord is floating. Once in, formulary drug can be infused into the CSF in one session via the needle, or over a week through a soft catheter. For long term infusion over months or years, the soft catheter is connected under the skin to a refillable programmable pump that is usually implanted under he abdominal skin.

In addition to being a novel, unique, efficacious and safe formulation for intrathecal administration, this formulation is also superior for intravenous or intra-arterial administration. The absence of systematic neurotoxic castor oil derivatives will reduce the well-known neurological complications. The tissue penetrating capabilities of DMSO will facilitate penetration of the blood-brain barrier by cyclosporin to come into contact with neurons to make it work better.

Medicament and Administration.

The formulary drag can be administration by the routes including oral, sublingual, buccal, nasal, inhalation, parenteral (including intraperitoneal, intraorgan, subcutaneous, intradermal, intramuscular, intra-articular, venous (central, hepatic or peripheral), lymphatic, cardiac, arterial, including selective or superselective cerebral arterial approach, retrograde perfusion through cerebral venous system, via catheter into the brain parenchyma or ventricles), direct exposure or under pressure onto or through the brain or spinal tissue, or any of the cerebrospinal fluid ventricles, injections into the subarachnoid, brain cisternal, subdural or epidural spaces, via brain cisterns or lumbar puncture, intra and peri-ocular instillation including application by injection around the eye, within the eyeball, its structures and layers, as well as via enteral, bowel, rectal, vaginal, urethral or bladder cisternal. Also for in utero and perinatal indications then injections into the maternal vasculature, or through or into maternal organ including the uterus, cervix and vagina, and into embryo, fetus, neonate and allied tissues and spaces such as the amniotic sac, the umbilical cord, the umbilical artery or veins and the placenta, with parenteral being the preferred route.

The formulary drug, containing cyclosporin dissolved in DMSO, for administration into the brain and related structures, spinal cord and related structures, ventricular system and cerebrospinal fluid spaces can be manufactured and distributed containing, aqueous and non-aqueous injection solutions, other pharmaceutically active compounds, additives including anti-oxidants, bacteriostats and solutes and sugars such as mannitol to make the formulary drug isotonic, hypotonic or hypertonic with the cerebrospinal fluid; and also aqueous and non-aqueous sterile suspensions. The formulary drug can be manufactured and distributed in unit-dose or multi-dose containers, such as sealed glass or plastic ampoules, vials, bottles and bags as a liquid, and in a dry state requiring the addition of DMSO.

The formulary drug for parenteral administration can be manufactured from cyclosporin, DMSO, aqueous sterile injection solutions, other pharmaceutically active compounds, additives including anti-oxidants, bacteriostats and solutes and sugars such as mannitol to make the formulary drug isotonic, hypotonic or hypertonic with the fluids of the recipient. The formulary drug can be manufactured and distributed in unit-dose or multi-dose containers, such as sealed glass or plastic ampoules, vials, bottles and bags as a liquid, and in a dry state requiring the addition of DMSO.

The formulations are used in patients who require neuroprotection from neurological diseases of acute to chronic nature including stroke, brain hemorrhage, brain and spine trauma, ionizing radiation, neurotoxicity to vestilbulocochlear structures, retinal detachment and neurodegeneration including amyotrophic lateral sclerosis, Parkinson's and Alzheimer's.

The formulations are used in patients who require both neuroprotection from neurological disease and that their neuro-axis be immunocompromised, such as in neural transplantation, neural xenotransplantation, multiple sclerosis, HIV neuropathy and Guillain-Barré syndrome.

The formulations are used in patients who require that they be immunocompromised, such as in transplantation and autoimmune disease.

The formulations are used for topical application for patients who require immunocompromise of the skin for diseases such such as psoriasis.

The formulary drug generally contains from 0.1 to 90% of the treatment medication by weight of the total composition. Cerebrospinal doses between 5 mg and 5 gram per day are possible, with about 50–150 mg/day for chronic administration, and 100–1000 mg/day for acute administration being preferable. Amounts of from 0.0001 mg to 200 mg/kg, or preferably 0.001 to 50 mg/kg, of body weight per day for parenteral administration and 0.001 to 150 mg/kg orally, can be given. Nevertheless, it could be necessary to alter those dosage rates, depending on the condition, weight, and individual reaction of the subject to the treatment, and the mode in which the administration is carried out, and the stage of the disease process or interval of administration. It may thus be sometimes adequate to use less than the before stated minimum dose, while in other instances the upper limit must be surpassed to obtain therapeutic results.

EXAMPLES

Example 1

Sterile Injectable Concentrate Formulary Drug with cyclosporin as active ingredient Containing per ml:

| | |
|---|---|
| Cyclosporin A | 200 mg |
| DMSO | 800 mg |

The formulary drag is made by dissolving 5 grams of cyclosporin into 20 grams dimethyl sulfoxide at room temperature. The solution thus obtained is made up to 25 ml with water. The solution is homogenized with stirring and filtered. The liquid is sterilized by radiation and then placed in a sealed container such as glass under inert gas atmosphere in doses of 1, 5 or 25 ml.

Sterile injectable concentrate formulary drug is administered, with or without dilution with for example isotonic saline, by infusion or by injection into cerebrospinal fluid spaces, brain, spine, vein or artery.

Example 2

A person in need of acute brain or spinal neuroprotection from trauma or stroke has the composition of example 1 injected into the cerebrospinal fluid of the ventricle of the brain through a burrhole in the skull, or into the cerebrospinal fluid of thecal sac via a lumbar puncture needle, or injected intravascularly.

Example 3

A person in need of chronic brain or spinal neuroprotection from neurodegenerative disease such as Parkinson's, Alzheimer's or amyotrophic lateral sclerosis has the composition of example 1 injected periodically by a reservoir or pump into the cerebrospinal fluid of a brain ventricle through a burrhole in the skull, or into the cerebrospinal fluid of the thecal sac via a lumbar catheter connected to a reservoir and pump.

Example 4

A person in need of neural immunosuppression for neural transplantation, neural xenotransplantation, or diseases with auto immune components like multiple sclerosis, Guillain-Barré, has the composition of example 1 injected periodically by a reservoir or pump into the cerebrospinal fluid of a ventricle of the brain through a burrhole in the skull, or into the cerebrospinal fluid of the spinal thecal sac via a lumbar catheter connected to a reservoir and pump.

Example 5

A person in need of systemic immunosuppression has intravenous injections or oral consumption of the compositions of examples 1.

INDUSTRIAL APPLICABILITY

From the above description it will be evident that the present invention provides improved compositions for the administration of cyclosporin. Additionally the present invention provides a completely new composition suitable for administration directly into the new target of delivery, the cerebrospinal fluid to directly treat diseases of the brain, which previously described compositions are not suitable for, because of the neurotoxicity of their solvents.

No precipitation was observed with an initial one month of testing of composition prepared according to example 1. Ampoules stored in darkness containing 5 ml stored at 0, 30, and 60 degrees C. show neither discoloration nor precipitation.

Rats receiving intraventricular cerebrospinal infusions showed no neurotoxicity, seizures or untoward effects. In addition, rats receiving injections intravenously showed no ill effects.

What is claimed is:

1. A method for administering cyclosporin into cerebrospinal fluid or cerebrospinal fluid spaces of a patient, which comprises:
   providing a sterile injectable solution of cyclosporin dissolved in DMSO in a pharmaceutically acceptable carrier, and
   administering said cyclosporin and DMSO sterile injectable solution by injection into a cerebrospinal fluid or cerebrospinal fluid spaces of said patient,
   wherein the concentration of cyclosporin is from 0.1% to 20% by weight of the total composition, and wherein DMSO is present in at least 80% by weight of the total composition.

2. A method for administering a sterile injectable solution of cyclosporin to a patient, which comprises:

providing a sterile injectable solution of cyclosporin dissolved in DMSO in a pharmaceutically acceptable carrier, and administering said sterile injectable solution of cyclosporin and DMSO to said patient by intravestibular injection, into or adjacent to the brain, or into or adjacent to the spinal cord of said patient, wherein the concentration of cyclosporin is from 0.1% to 20% by weight of the total composition, and wherein DMSO is present in at least 80% by weight of the total composition.

3. A method for administering cyclosporin by injection into a patient, which comprises:

providing a sterile injectable solution of cyclosporin dissolved in DMSO in a pharmaceutically acceptable carrier, and administering said sterile injectable solution of cyclosporin and DMSO by injection into an intravenous, intra-arterial or intraparenchymal spaces of said patient, wherein the concentration of cyclosporin is from 0.1% to 20% by weight of the total composition, and wherein DMSO is present at least 80% by weight in the composition.

4. A method for administering cyclosporin inhalationally or nasally to a patient, which comprises:

providing the cyclosporin dissolved in DMSO in a pharmaceutically acceptable solution, and administering said cyclosporin and DMSO solution inhalationally or nasally to said patient, wherein the concentration of cyclosporin is from 0.1% to 20% by weight of the total composition, and wherein DMSO is present at least 80% by weight in the composition.

5. The method according to claim 1 wherein the administration of a sterile injectable solution of cyclosporin into said cerebrospinal fluid space is intraventricular or intrathecal.

6. The method of claim 1, 2, 3 or 4 wherein the cyclosporin is cyclosporin A or a salt thereof.

7. A method of providing neuroprotection to a patient in need thereof for treating Alzheimer's disease, Parkinson's disease, amyotrophic lateral sclerosis, multiple sclerosis, HIV neuropathy, Guillain-Barre' syndrome, neural transplantation, neural xenotransplantation, stroke, brain hemorrhage, brain and spine trauma, ionizing radiation, neurotoxicity of vestibular structures, or retinal detachment, which comprises administering a sterile injectable solution of cyclosporin dissolved in DMSO according to the method of claim 1, 2, 3 or 4 in a pharmaceutically acceptable carrier to said patient.

8. A method for inducing systemic immunosuppression in a patient of transplantation or autoimmune disease, which comprises administering a sterile injectable solution of cyclosporin and DMSO according to the method of claim 1, 2, 3 or 4 to said patient.

9. The method of claim 1, 2, 3 or 4 wherein a dose of from 0.0001 to 200 mg/kg/day of cyclosporin is administered.

10. The method of claim 1, 2, 3 or 4 wherein a dose of from 5 to 5000 mg/day of cyclosporin is administered.

* * * * *

UNITED STATES PATENT AND TRADEMARK OFFICE
CERTIFICATE OF CORRECTION

| | | |
|---|---|---|
| PATENT NO. | : 7,446,093 B1 | Page 1 of 1 |
| APPLICATION NO. | : 09/674092 | |
| DATED | : November 4, 2008 | |
| INVENTOR(S) | : Marcus Keep et al. | |

It is certified that error appears in the above-identified patent and that said Letters Patent is hereby corrected as shown below:

Title page the line reading Item "(22) PCT Filed: Feb. 26, 2000" should read --(22) PCT Filed: Feb. 26, 1999--

The line reading "§ 371 (c)(1), (2), (4) Date: Aug. 26, 2002" should read --§ 371 (c)(1), (2), (4) Date: Feb. 27, 2001--

Signed and Sealed this

Sixth Day of April, 2010

David J. Kappos
*Director of the United States Patent and Trademark Office*